United States Patent [19]

Hoffman, Jr. et al.

[11] Patent Number: 4,946,859
[45] Date of Patent: Aug. 7, 1990

[54] 4-(2-METHYL-2-HYDROXY-PROPYLAMINO)-5,6-DIHYDROTHIENO-[2,3-B]THIOPYRAN-2-SULFONAMIDE-7,7-DIOXIDE

[75] Inventors: Jacob M. Hoffman, Jr., North Wales; Ling L. Lee, Lansdale; Sandor L. Varga, Harleysville; Anthony G. Zacchei, Ambler, all of Pa.

[73] Assignee: Merck & Co., Inc., Rahway, N.J.

[21] Appl. No.: 387,033

[22] Filed: Jul. 31, 1989

[51] Int. Cl.$^5$ .................... C07D 495/04; A61K 31/38
[52] U.S. Cl. ....................................... 514/432; 549/23
[58] Field of Search ........................... 549/23; 514/432

[56] References Cited

U.S. PATENT DOCUMENTS 4,677,115  6/1987  Baldwin et al. ...................... 514/432
4,797,413  1/1989  Baldwin et al. ...................... 514/432

Primary Examiner—Mary C. Lee
Assistant Examiner—Jacqueline Haley
Attorney, Agent, or Firm—William H. Nicholson; Joseph F. DiPrima

[57] ABSTRACT 4-(2-Methyl-2-hydroxypropylamino)-5,6-dihydro-thieno[2,3-b]thiopyran-2-sulfonamide-7,7-dioxide is a major mammalian metabolite of 4-(2-methylpropylamino)-5,6-dihydrothieno[2,3-b]thiopyran-2-sulfonamide-7,7-dioxide and is itself an active carbonic anhydrase inhibitor useful in the treatment of ocular hypertension by topical administration.

3 Claims, No Drawings

4-(2-METHYL-2-HYDROXYPROPYLAMINO)-5,6-DIHYDROTHIENO-[2,3-B]THIOPYRAN-2-SULFONAMIDE-7,7-DIOXIDE

SUMMARY OF THE INVENTION

This invention relates to the novel compound of structural formula:

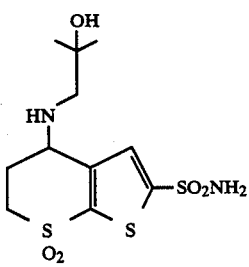

as well as the pharmaceutically and ophthalmologically acceptable salts thereof. This invention also relates to pharmaceutical compositions and the use thereof for systemic and ophthalmic use employing the novel compound of this invention as active ingredient for the treatment of elevated intraocular pressure, especially when accompanied by pathological damage such as in the disease known as glaucoma.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many β-adrenergic blocking agents are effective in reducing intraocular pressure. While many of these agents are effective in reducing intraocular pressure, they also have other characteristics, e.g. membrane stabilizing activity, that are not acceptable for chronic ocular use. (S)-1-tert-Butylamino-[(4-morpholino-1,2,5-thiadiazol-3-yl)oxy]-2-propanol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

Although pilocarpine, physostigmine and the β-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in U.S. Pat. Nos. 4,386,098; 4,416,890; and 4,426,388. The compounds reported therein are 5 (and 6)-hydroxy-2-benzothiazolesulfonamides and acyl esters thereof.

More recently, U.S. Pat. Nos. 4,677,115 and 4,797,413 and U.S. application with Attorney Docket No. 17905 filed concurrently herewith describe topically effective carbonic anhydrase inhibitors which also are thieno[2,3-b]thiopyran-2-sulfonamides.

DETAILED DESCRIPTION OF THE INVENTION

The novel compound of this invention has structural formula:

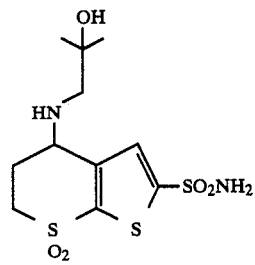

or a pharmaceutically acceptable salt thereof.

The novel compound of this invention was originally isolated from rat urine and erythrocytes following chronic oral dosing with MK-0927 at dosage levels of 50 and 100 mg/kg/day. The compound was isolated from the biological matrix by selective solvent extraction under alkaline conditions and purified by repetitive HPLC techniques using different mobile phase conditions. The structure of the metabolite was tentatively assigned based upon derivatization reactions, chromatographic properties, NMR analyses and MS analysis. Unequivocal proof of structure was attained upon comparison of the aforementioned properties with those of the subsequently synthesized material (vide infra). Further studies with a homochiral reagent established that the major enantiomeric composition of the metabolite in the erythrocyte possessed the (+)-configuration. In addition, this metabolite has also been isolated and quantitated in rhesus monkey urine and erythrocytes following single and multiple dosing at doses of 2, 15 and 100 mg/kg/day.

The compound is synthesized by treatment of the unsubstituted amine with isobutylene oxide in a lower alkanol such as methanol in a closed system at 60°-70° C. for about ~18 hours.

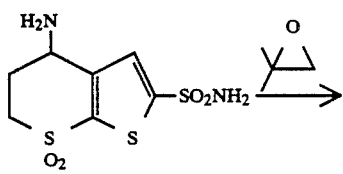

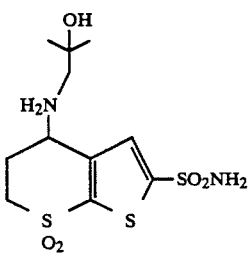

This invention is also concerned with formulations adapted for topical ocular administration in the form of solutions, gellable solutions, ointments, solid water soluble inserts or gels for the treatment of glaucoma and other stages of elevated intraocular pressure and contain about 0.1% to 15% by weight of medicament, especially about 0.5 to 2% by weight of medicament, the remainder being comprised of carriers and other excipients well known in the art.

The medicament in the novel topical ocular formulations comprises the novel compound of this invention either alone or in combination with a β-adrenergic blocking agent such as timolol maleate or a parasympathomimetic agent such as pilocarpine. In such combinations the two active agents are present in approximately equal amounts.

The novel method of treatment of this invention comprises the treatment of elevated introacular pressure by the administration of the novel compound of this invention or a pharmaceutical formulation thereof. Of primary concern is the treatment by topical ocular administration of about 0.1 to 25 mg and especially 0.2 to 10 mg of such compound per day, either by single dose or on a 2 to 4 dose per day regimen.

EXAMPLE 1

Preparation of 4-(2-Methyl-2-hydroxypropylamino)-5,6-dihydro-thieno[2,3-b]-thiopyran-2-sulfonamide-7,7-dioxide hydrochloride A suspension of racemic 4-amino-5,6-dihydro-thieno[2,3-b]thiopyran-2-sulfonamide-7,7-dioxide (1.129 g, 4.0 mmol) in methanol (10 mL) containing isobutylene oxide (2.5 mL, 30 mmol) was sealed in a screw-top tube and warmed at 60°-80° C. for 18 hours. The cooled suspension was filtered giving nearly pure product (1.2 gm). This material was chromatographed on silical gel and separated by gradient elution with 10-15% methanol/chloroform containing 1% ammonium hydroxide. The purified product (948 mg) was suspended in ethanol (10 mL) and treated with excess ethanolic HCl. This suspension was warmed to give a clear solution and upon cooling the racemic hydrochloride salt crystallized out (987 mg, 63% yield), mp 227°-228° C. decomposition.

Analysis calculated for $C_{11}H_{18}N_2O_5S_3 \cdot HCl$: N-7.17, C-33.79, H-4.90. Found: N-7.04, C-33.91, H-4.98.

EXAMPLE 2

| Active ingredient | 1 mg | 15 mg |
|---|---|---|
| Monobasic sodium phosphate 2H$_2$O | 9.38 mg | 6.10 mg |
| Dibasic sodium phosphate .12H$_2$O | 28.48 mg | 16.80 mg |
| Benzalkonium chloride | 0.10 mg | 0.10 mg |
| Water for injection q.s. and. | 1.0 ml | 1.0 ml |

The novel compound, phosphate buffer salts, and benzalkonium chloride are added to and dissolved in water. The pH of the composition is adjusted to 6.8 and diluted to volume. The composition is rendered sterile by ionizing radiation.

EXAMPLE 3

| Active ingredient | 5 mg |
|---|---|
| petrolatum q.s. and. | 1 gram |

The compound and the petrolatum are aseptically combined.

EXAMPLE 4

| Active ingredient | 1 mg |
|---|---|
| Hydroxypropylcellulose q.s. | 12 mg |

Ophthalmic inserts are manufactured from compression molded films which are prepared on a Carber Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

What is claimed is:

1. A compound of structural formula:

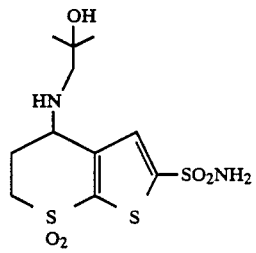

2. An ophthalmological formulation for the treatment of ocular hypertension comprising an ophthalmologically acceptable carrier and an effective ocular antihypertensive amount of a compound of claim 1.

3. A method of treating elevated intraocular pressure comprising the administration to a patient in need of such treatment of an effective introacular pressure lowering amount of the compound of claim 1.

* * * * *